(12) United States Patent
Obach et al.

(10) Patent No.: US 6,239,147 B1
(45) Date of Patent: May 29, 2001

(54) 1-TRIFLUOROMETHYL-4-HYDROXY-7-PIPERIDINYL-AMINOMETHYLCHROMAN DERIVATIVES

(75) Inventors: R. Scott Obach, Gales Ferry; Douglas Alan Scully, Noank, both of CT (US)

(73) Assignee: Pfizer INC, New York, NY (US)

( * ) Notice: Subject to any disclaimer, the term of this patent is extended or adjusted under 35 U.S.C. 154(b) by 0 days.

(21) Appl. No.: 09/572,213

(22) Filed: May 17, 2000

Related U.S. Application Data

(60) Provisional application No. 60/135,399, filed on May 21, 1999.

(51) Int. Cl.[7] ............... A61K 31/445; C07D 405/12
(52) U.S. Cl. ............................. 514/320; 546/196
(58) Field of Search ............... 514/320; 546/196

(56) References Cited

U.S. PATENT DOCUMENTS

| | | | |
|---|---|---|---|
| 5,604,247 | * 2/1997 | Von Sprecher et al. | 514/320 |
| 5,646,144 | 7/1997 | Schilling et al. | 514/241 |
| 5,886,011 | * 3/1999 | Tanoue et al. | 514/320 |
| 5,935,972 | * 8/1999 | Naylor et al. | 514/320 |

FOREIGN PATENT DOCUMENTS

| | | | |
|---|---|---|---|
| 0826684 | 3/1998 | (EP) | C07D/405/12 |
| 9506645 | 3/1995 | (WO) | C07D/307/79 |
| 9703066 | 1/1997 | (WO) | C07D/401/12 |
| 9708144 | 3/1997 | (WO) | C07D/211/56 |
| 9925714 | 5/1999 | (WO) | C07D/405/12 |

* cited by examiner

*Primary Examiner*—Ceila Chang
(74) *Attorney, Agent, or Firm*—Peter C. Richardson; Paul H. Ginsburg; Roy F. Waldron

(57) ABSTRACT

This invention relates to novel 1-trifluoromethyl-4-hydroxy-7-piperidinylaminomethylchroman derivatives of the formula

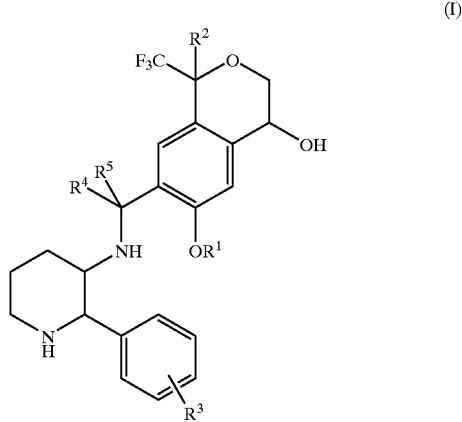

(I)

wherein $R^1$ is $C_1$–$C_6$ alkyl;
$R^2$ is hydrogen, $C_1$–$C_6$ alkyl, halo $C_1$–$C_6$ alkyl or phenyl;
$R^3$ is hydrogen or halo; and
$R^4$ and $R^5$ are independently hydrogen, $C_1$–$C_6$ alkyl or halo $C_1$–$C_6$ alkyl,
their pharmaceutically acceptable salts, pharmaceutical compositions containing such compounds, and the use of such compounds to treat CNS, gastrointestinal and other disorders.

8 Claims, No Drawings

1-TRIFLUOROMETHYL-4-HYDROXY-7-PIPERIDINYL-AMINOMETHYLCHROMAN DERIVATIVES

This application claims priority of Provisional Application No. 60/135,399 filed May 21, 1999.

This invention relates to novel 1-trifluoromethyl-4-hydroxy-7-piperidinylaminomethylchroman derivatives and their pharmaceutically acceptable salts, pharmaceutical compositions containing such compounds, and the use of such compounds as substance P antagonists.

BACKGROUND

Substance P is a naturally occurring undecapeptide belonging to the tachykinin family of peptides, the latter being so-named because of their prompt stimulatory action on smooth muscle tissue. More specifically, substance P is a pharmaceutically active neuropeptide that is produced in mammals (having originally been isolated from the gut) and possesses a characteristic amino acid sequence as illustrated by D. F. Veber et al. in U.S. Pat No. 4,680,283. The wide involvement of substance P and other tachykinins in the pathophysiology of numerous diseases has been amply demonstrated in the art. For instance, substance P has recently been shown to be involved in the transmission of pain or migraine, as well as in central nervous system disorders such as anxiety and schizophrenia, in respiratory and inflammatory diseases such as asthma and rheumatoid arthritis, respectively, and in gastrointestinal disorders and diseases of the GI tract, like ulcerative colitis, irritable bowel syndrome, Crohn's disease, etc. It is also reported that tachykinin antagonists are useful for the treatment of cardiovascular diseases, allergic conditions, immunoregulation, vasodilation, bronchospasm, reflex or neuronal control of the viscera, senile dementia of the Alzheimer type, emesis, sunburn and *Helicobacter pylori* infection.

European Patent Application 840,732, which was published on May 13, 1998 and international Patent Application PCT/IB97/01466, filed on Nov. 19, 1997, disclose a variety of substituted piperidine compounds, including piperidine compounds having a substituent comprising a fused ring moiety including an oxygen atom, as substance P antagonists.

Substance P antagonists having improved activity and fewer side effects are desired.

BRIEF DESCRIPTION OF THE INVENTION

The present invention provides piperidinylaminomethyl trifluoromethyl cyclic ether compounds of the following chemical formula (I):

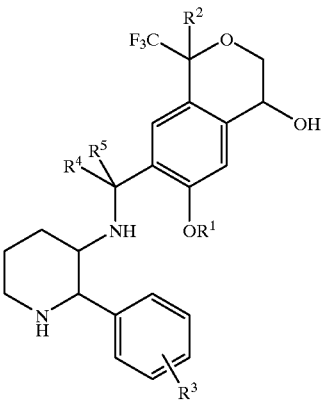

(I)

and their pharmaceutically acceptable salts, wherein
$R^1$ is $C_1$–$C_6$ alkyl;
$R^2$ is hydrogen, $C_1$–$C_6$ alkyl, halo $C_1$–$C_6$ alkyl or phenyl;
$R^3$ is hydrogen or halo; and
$R^4$ and $R^5$ are independently hydrogen, $C_1$–$C_6$ alkyl or halo $C_1$–$C_6$ alkyl.

The compounds of formula (I) contain at least two chiral centers and therefore exist as at least two diastereoisomeric pairs of optical isomers including epimers. This invention includes both the individual isomers of the compounds of formula (I) and mixtures of two or more of such isomers.

The compounds of formula (I) of the invention preferably have the (2S,3S) configuration with respect to the piperidine ring.

Embodiments of the invention are compounds of formula (I) wherein $R^1$ is $C_1$–$C_3$ alkyl; $R^2$ is hydrogen, $C_1$–$C_3$ alkyl, halo $C_1$–$C_3$ alkyl or phenyl; $R^3$ is hydrogen or fluorine; and $R^4$ and $R^5$ are independently hydrogen, $C_1$–$C_3$ alkyl or halo $C_1$–$C_3$ alkyl.

Other embodiments of the invention are compounds of formula (I) wherein $R^1$ is methyl; $R^2$ is hydrogen, methyl, trifluoromethyl or phenyl; $R^3$ is hydrogen; and $R^4$ and $R^5$ area hydrogen.

A specific preferred compound of the formula (I) is (2S,3S)-3-(6-methoxy-1-methyl-1-trifluoromethylisochroman-7-yl)methylamino-2-phenylpiperidine or a pharmaceutically acceptable salt thereof.

The compounds of the invention are useful as substance P antagonists, and thus useful for treating a disorder or condition selected from dysthymia, major depressive disorder, pediatric depression, generalized anxiety disorder, obsessive-compulsive disorder, panic disorder, phobias such as social phobia and agoraphobia; post traumatic stress disorder, borderline personality disorder, acute pain, chronic pain, migraine, angiogenesis, sunburn, urinary incontinence, inflammatory disorders such as rheumatoid arthritis, osteoarthritis, psoriasis, asthma and allergic disorders; emesis, including acute, delayed and anticipatory emesis wherein the emetic agent or condition is chemotherapy, radiation, surgery, motion, migraine or any other emetic agent or condition; disorders caused by *Helicobacter pylori*, cardiovascular disorders, ophthalmic disorders, inflammation of the urinary tract, psychosis, schizophrenia, conduct disorder, disruptive behavior disorder, bipolar disorder, movement disorders such as Tourette's syndrome, akinetic-rigid syndrome, movement disorders associated with Parkinson's disease, tardive dyskinesia and other dyskinesias;

cognitive disorders such as dementias (including age related dementia and senile dementia of the Alzheimer's type) and memory disorders (e.g., amnestic disorders), eating disorders such as anorexia nervosa and bulimia nervosa, attention deficit hyperactivity disorder, chronic fatigue syndrome, premature ejaculation, premenstrual syndrome, premenstrual dysphoric disorder, chemical dependencies and addictions, stress related somatic disorders, neuralgia, peripheral neuropathy, gastroesophageal reflux disease, reflex sympathetic dystrophy such as shoulder/hand syndrome; hypersensitivity disorders such as to poison ivy; fibromyalgia, angina, Reynaud's disease, rheumatic diseases such as fibrositis; eczema, rhinitis, allergies, post-herpetia neuralgia, cystitis, inflammatory bowel disease, irritable bowel syndrome, colitis, fibrosing and collagen disorders such as scleroderma and eosinophilic fascioliasis; blood flow disorders due to vasodilatation, and disorders related to immune enhancement or suppression such as systemic lupus erythematosus in a mammal, especially a human. These compounds are especially useful as anti-inflammatory or anti-emetic agents, or agents for treating CNS disorders.

The compounds of the invention are particularly useful in the treatment of emesis, including acute, delayed or anticipatory emesis such as emesis or nausea induced by chemotherapy, radiation, surgery, pregnancy, motion, vestibular disorders, toxins, migraine, and variations in intracranial pressure. Most specifically, these compounds are of use in the treatment of emesis induced by antineoplastic agents, including those used in cancer therapy, and emesis induced by other pharmacological agents such as rolipram or morphine. These compounds are also useful for chronic and acute pain including hyper-analgesic pain, neuropathic pain, post-operative pain and pain associated with nerve damage.

The present invention also relates to a pharmaceutical composition for treating a disorder or condition for which antagonist activity toward substance P is needed, in an mammal, which comprises an amount of the compound of formula (I), or a pharmaceutically acceptable salt thereof, that is effective in treating such disorder or condition, and a pharmaceutically acceptable carrier.

The invention also relates to a method of treating a disorder or condition for which antagonist activity toward substance P is needed, in a mammal, which comprises administering to a mammal in need of such treatment an amount of a compound of formula (I), or a pharmaceutically acceptable salt thereof, that is effective in treating such disorder or condition.

The invention also relates to a pharmaceutical composition for treating a disorder or condition selected from dysthymia, major depressive disorder, pediatric depression, generalized anxiety disorder, obsessive-compulsive disorder, panic disorder, phobias such as social phobia and agoraphobia; post traumatic stress disorder, borderline personality disorder, acute pain, chronic pain, migraine, angiogenesis, sunburn, urinary incontinence, inflammatory disorders such as rheumatoid arthritis, osteoarthritis, psoriasis, asthma and allergic disorders; emesis, including acute, delayed and anticipatory emesis wherein the emetic agent or condition is chemotherapy, radiation, surgery, motion, migraine or any other emetic agent or condition; disorders caused by *Helicobacter pylori,* cardiovascular disorders, ophthalmic disorders, inflammation of the urinary tract, psychosis, schizophrenia, conduct disorder, disruptive behavior disorder, bipolar disorder, movement disorders such as Tourette's syndrome, akinetic-rigid syndrome, movement disorders associated with Parkinson's disease, tardive dyskinesia and other dyskinesias; cognitive disorders such as dementias (including age related dementia and senile dementia of the Alzheimer's type) and memory disorders (e.g., amnestic disorders), eating disorders such as anorexia nervosa and bulimia nervosa, attention deficit hyperactivity disorder, chronic fatigue syndrome, premature ejaculation, premenstrual syndrome, premenstrual dysphoric disorder, chemical dependencies and addictions, stress related somatic disorders, neuralgia, peripheral neuropathy, gastroesophageal reflux disease, reflex sympathetic dystrophy such as shoulder/hand syndrome; hypersensitivity disorders such as to poison ivy; fibromyalgia, angina, Reynaud's disease, rheumatic diseases such as fibrositis; eczema, rhinitis, allergies, post-herpetia neuralgia, cystitis, inflammatory bowel disease, irritable bowel syndrome, colitis, fibrosing and collagen disorders such as scleroderma and eosinophilic fascioliasis; blood flow disorders due to vasodilatation, and disorders related to immune enhancement or suppression such as systemic lupus erythematosus in a mammal, especially a human, comprising an amount of the compound of formula (I), or a pharmaceutically acceptable sail thereof, that is effective in treating such disorder or condition, and a pharmaceutically acceptable carrier.

The invention also relates to a method of treating a disorder or condition selected from dysthymia, major depressive disorder, pediatric depression, generalized anxiety disorder, obsessive-compulsive disorder, panic disorder, phobias such as social phobia and agoraphobia; post traumatic stress disorder, borderline personality disorder, acute pain, chronic pain, migraine, angiogenesis, sunburn, urinary incontinence, inflammatory disorders such as rheumatoid arthritis, osteoarthritis, psoriasis, asthma and allergic disorders; emesis, including acute, delayed and anticipatory emesis wherein the emetic agent or condition is chemotherapy, radiation, surgery, motion, migraine or any other emetic agent or condition; disorders caused by *Helicobacter pylori,* cardiovascular disorders, ophthalmic disorders, inflammation of the urinary tract, psychosis, schizophrenia, conduct disorder, disruptive behavior disorder, bipolar disorder, movement disorders such as Tourette's syndrome, akinetic-rigid syndrome, movement disorders associated with Parkinson's disease, tardive dyskinesia and other dyskinesias; cognitive disorders such as dementia (including age related dementia and senile dementia of the Alzheimer's type) and memory disorders (e.g., amnestic disorders), eating disorders such as anorexia nervosa and bulimia nervosa, attention deficit hyperactivity disorder, chronic fatigue syndrome, premature ejaculation, premenstrual syndrome, premenstrual dysphoric disorder, chemical dependencies and addictions, stress related somatic disorders, neuralgia, peripheral neuropathy, gastroesophageal reflux disease, reflex sympathetic dystrophy such as shoulder/hand syndrome; hypersensitivity disorders such as to poison ivy; fibromyalgia, angina, Reynaud's disease, rheumatic diseases such as fibrositis; eczema, rhinitis, allergies, post-herpetia neuralgia, cystitis, inflammatory bowel disease, irritable bowel syndrome, colitis, fibrosing and collagen disorders such as scleroderma and eosinophilic fascioliasis; blood flow disorders due to vasodilatation, and disorders related to immune enhancement or suppression such as systemic lupus erythematosus in a mammal, especially a human, comprising administering to a mammal in need of such treatment an amount of a compound of formula (I), or a pharmaceutically acceptable salt thereof, that is effective in preventing or treating such disorder or condition.

The term "treating" as used herein refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

The term "halo" means F, Cl, Br and I, preferably Cl or F.

The term "alkyl" as used herein refers to straight or branched chain saturated radicals, including, but not limited to methyl, ethyl, n-propyl, isopropyl, and t-butyl.

The term "halo $C_1$–$C_6$ alkyl" is used herein to mean a straight, branched or cyclic $C_1$–$C_6$ alkyl substituted by one or more (preferably one to seven) halo. These compounds include, but are not limited to, trifluoromethyl, difluoroethyl, trifluoroethyl, pentafluoroethyl, trifluoroisopropyl, tetrafluoroisopropyl, pentafluoroisopropyl, hexafluoroisopropyl, and the like.

DETAILED DESCRIPTION OF THE INVENTION

The piperidinylaminomethyl trifluoromethyl cyclic ether compounds of formula (I) of the invention may be prepared as described in the following reaction schemes and discussion. Unless otherwise indicated, in the reaction schemes and discussion that follow, $R^1$, $R^2$, $R^4$, and $R^5$ are defined as above, and Z represents hydrogen or amino protecting group.

Scheme 1 illustrates a method for preparation of a compound of formula (VI), which can then be converted into the corresponding metabolites of the formula (I) via the biotransformation methods described below. Compounds of the formula (VI) can be prepared by reductive alkylation of compound (II) with compound (III).

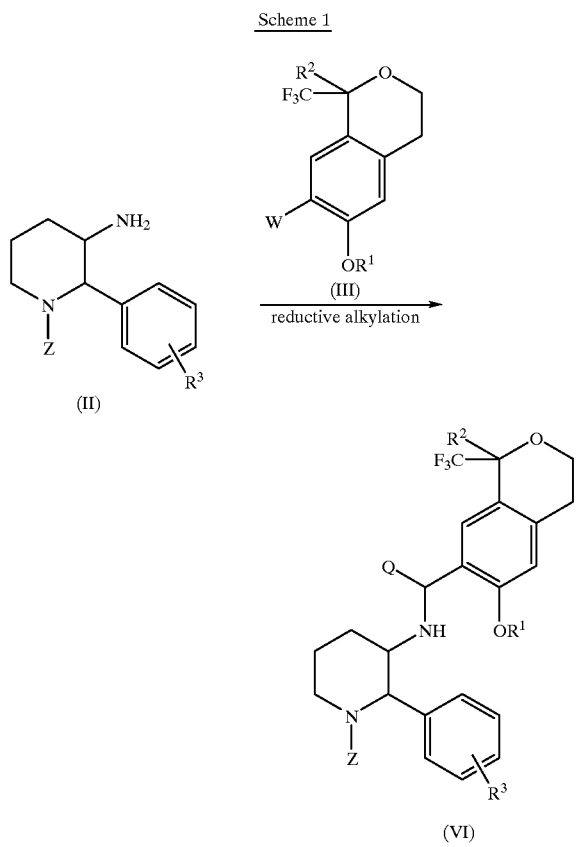

A compound of formula (VI) wherein Z is hydrogen or an amino protecting group and Q is $R^4$ or $R^5$ as defined above, can be synthesized by reductive alkylation of an amine compound of formula (II) with a compound of formula (III) according to the known procedures as described in the International Patent Publication No. WO 97/03066. The reaction can be carried out in the presence of a suitable reducing reagent in a reaction inert solvent. The suitable reducing reagents are, for example, borohydrides such as sodium triacetoxyborohydride ($NaB(OAc)_3H$), sodium borohydride ($NaBH_4$) and sodium cyano borohydride ($NaBH_3CN$), boranes, lithium aluminum hydride ($LiAlH_2$), and trialkylsilanes. The suitable solvents include polar solvents such as methanol, ethanol, methylene chloride, tetrahydrofuran (THF), dioxane and ethyl acetate. The reaction can be conducted at from about $-78°$ C. to the reflux temperature of the solvent, preferably from 0 to $25°$ C. for 5 minutes to 48 hours, preferably 0.5 to 12 hours. Preferably, compounds (VI), wherein Q is other than hydrogen, can be obtained by reacting compound (II) with compound (III) wherein W is an appropriate acyl group. This reaction can be carried out in the presence of a reducing agent such as $NaBH_3CN$ and a Lewis acid such as tin(IV) chloride ($TiCl_4$) in a reaction inert solvent such as dichloromethane (*Tetrahedron Letter,* Vol. 31, p. 5547, 1990). When Z is an amino protecting group, the amino protecting group can be removed after the reductive alkylation using methods known to a person skilled in the art (see, e.g., *Protective Groups in Organic Synthesis,* T. W. Greene, et al., John Wiley & Sons, Inc., 1991), to obtain the compound of formula (VI). Specifically, when Z is ten-butoxycarbonyl (abbreviated as "Boc"), Boc can be removed in the presence of an acid such as HCl in a reaction inert solvent such as methanol under an inert atmosphere (e.g., under nitrogen atmosphere).

A starting material of formula (II) can be prepared by nitrogen protection of a(2S,3S)-3-amino-2-phenylpiperidine compound, which can be prepared by the known methods as described, for example, in the International Patent Publication No. WO 92/17449. The nitrogen protection of the piperidine ring of the compounds of formula (II) can be carried out according to known procedures as described in, for example, the International Patent Publication No. WO 97103066. Suitable protecting group are for example Boc (t-butoxycarbonyl), benzyloxycarbonyl (Cbz) or trifluoroacetyl. For example, nitrogen protection by Boc can be carried out by treating the (2S,3S)-3-amino-2-phenylpiperidine compound with (t-BuOCO)$_2$O in the presence of a base such as sodium hydroxide, sodium bicarbonate or triethylamine.

Compounds of formula (III) can be prepared by formylation or acylation of compounds of formula (IV) as illustrated in Scheme 2.

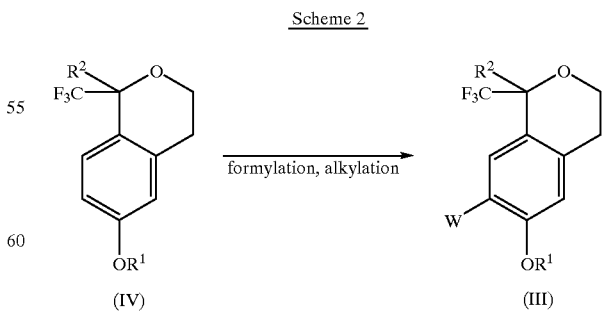

Known formylation or acylation methods can be used. For example, direct formylation may be accomplished by contacting compound (IV) with a suitable formylating agent in the presence of a suitable catalyst. Suitable formylating agent/catalyst systems include dichloromethyl methyl ether/titanium (IV) chloride ($CH_2CHOCH_3/TiCl_4$), trifluoroacetic acid ($CF_3CO_2H$)/hexamethylenetetramine (modified Duff's conditions) and phosphoryl trichloride ($POCl_3$) DMF (Vilsmeier's conditions). More specifically, the formylation of compound (IV) with $CH_2CHOCH_3/TiCl_4$ can be carried out in a reaction inert solvent under nitrogen atmosphere. Suitable solvents include dichloromethane and 1,2-dichloroethane at from about –120° C. to room temperature for about 10 minute to 10 hours, preferably –78° C. for 5 minutes to 4 hours. The Duff reaction can be also applied to the formylation in accordance with the reaction conditions disclosed in International Patent Publication WO 94/24081.

Also, a suitable indirect formylation method comprises (i) halogenating compound (IV), (ii) replacing the halogen atom by a cyano group, and then (iii) subjecting the resultant cyano-substituted compound to reduction. (i) The halogenation may be carried out according to the known procedures as reported by G. A. Olah et al. (*J. Org. Chem.*, Vol. 58, pp. 3194–, 1983). (ii) The replacement of the halogen atom with a cyano group can be achieved according to the known procedures as reported by D. M. Tschaem et al., (*Synth. Commun.*, Vol. 24, pp. 887–, 1994) or by K. Takagi et al, (*Bull. Chem. Soc. Jpn.*, Vol. 64, pp. 1118–, 1991). (iii) The reduction as used herein may be achieved in the presence of diisopropyl aluminium hydride (DIBAL-H) in dichloromethane or Raney Ni in formic acid.

The acylation can be achieved by well-known Friedel-Crafts acylation described for example in *Advanced Organic Chemistry* by Jerry March, John Wiley & Sons, forth edition, 1992, p. 539, and the references therein. More specifically, compound (IV) can be reacted with an acylating agent in the presence of an acid catalyst to give compound (III). Suitable acylating agents include acyl chloride, acyl fluoride and anhydrides, preferably acyl chloride. Suitable acid catalysts include sulfuric acid and Lewis acid such as aluminum chloride, preferably aluminum chloride. This reaction can typically be carried out at a temperature from about –10° C. to room temperature, for about 5 minutes to 2 hours, preferably at about 0° C. for about 1 hour.

A cyclic ether of formula (IV) can be prepared from a compound of formulae (Va) or (Vb) according to the known procedures as reported by W. E. Parham et al. (*J. Org. Chem.*, Vol. 39, pp. 2048, 1974) or the procedures illustrated in Scheme 3.

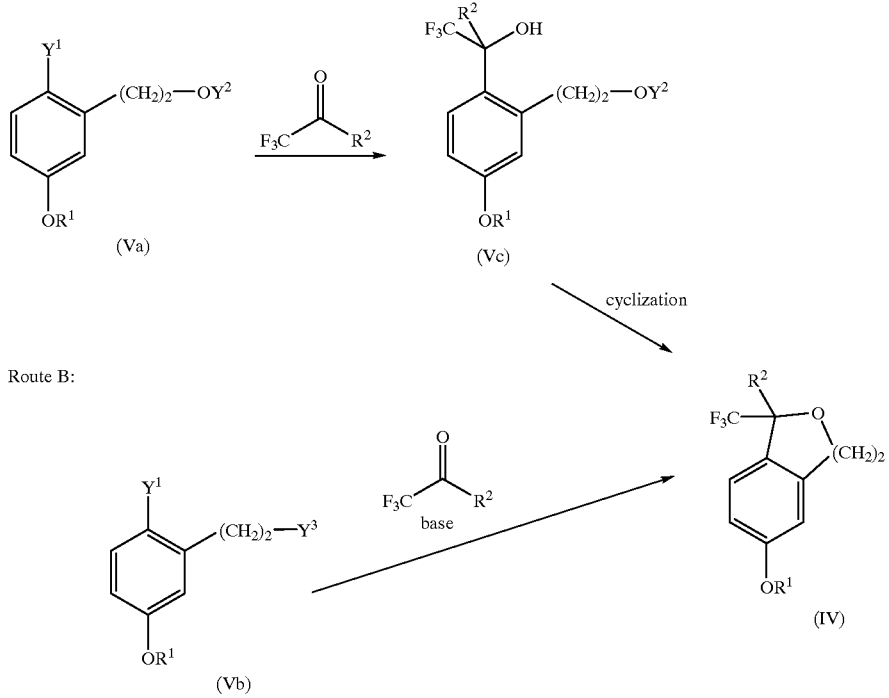

Scheme 3

In Route A of Scheme 3, a compound of formula (IV) can be synthesized from a compound of formula (Va) wherein $y^1$ is Br, I or Cl (preferably Br) and $Y^2$ is hydrogen or a hydroxy protecting group (suitably tetrahydropyranyl, abbreviated as "THP"). The compound of formula (Va) can be metallated by treatment with an organometallic compound. The reaction mixture can subsequently be treated with a carbonyl compound represented by $CF_3C(=O)R^2$ to give the diol (Vc). If required, the hydroxy protecting group $Y^2$ of the diol (Vc) can be removed. Then, the diol (Vc) can be subjected to cyclization to give the cyclic ether compound (IV).

The metallation of compound (Va) can be carried out in the presence of an organometallic compounds such as n-butyl lithium, sec-butyl lithium or tert-butyl lithium. The metallation and the subsequent reaction with $CF_3C(=O)R^2$ can be carried out in a reaction inert solvent such as THF, ether and hexane under an inert atmosphere, for example, under nitrogen, at from about –150° C. to room temperature for 15 minutes to 12 hours, preferably from –120° C. to –30° C. for 10 minutes to 6 hours. The hydroxy protection and deprotection with a protecting group $Y^2$ can be achieved under suitable conditions depending on the protecting group chosen according to known methods (see, e.g., *Protecting Group in Organic Synthesis* by T. W. Greene et al., published from John Wiley & Sons, Inc.).

The cyclization of the diol (Vc) can be carried out in the presence of an acid according to the known methods reported as by for example W. E. Parham et al. (*Synthesis, pp.* 116–, 1976) or D. Seebach et al. (*Chem. Ber.,* Vol. 116, pp. 8354–, 1994). Suitable acids are, for example, HCl, $H_2SO_4$ or p-toluenesulfonic acid trifluoro acetic acid (abbreviated as TFA). The reaction can be carried out at from about room temperature to about 200° C. for 10 minutes to 12 hours, preferably at 60° C. to 150° C. for 30 minutes to 6 hours.

Alternatively, the cyclization can be carried out according to the procedures known as Mitsunobu reaction or the procedures reported by J. R. Falck et al. (*J. Am. Chem. Soc.,* Vol. 116, pp. 8354–, 1994). For example, the Mitsunobu reaction can be carried out in the presence of triphenyl phosphine/diethyl azodicarboxylate in a suitable solvent such as dichloromethane under nitrogen at about 0° C. for from about 5 minutes to 6 hours.

In Route B of the Scheme 3, a cyclic ether compound of formula (IV) can be synthesized by subjecting a compound of formula (Vb), wherein $Y^3$ is a leaving group, to a one-step cyclization with $CF_3C(=O)R^2$ in the presence of a suitable base (see, e.g., *J. Org. Chem.,* Vol. 41, pp. 1184–, 1976). Suitable leaving groups include Cl, Br, tosylate, mesylate and triflate. Suitable bases include alkyl lithium such as n-BuLi, sec-BuLi or t-BuLi. For example, the reaction can be carried out first by treating a compound of formula (Vb) with n-BuLi in a suitable reaction inert solvent such as THF/hexane, under nitrogen at from about –120° C. to 0° C. for about 5 minutes to 12 hours, preferably –100° C. to –60° C. for 10 minutes to 6 hours. Subsequently, to the reaction mixture the carbonyl compound $CF_3C(=O)R^2$ can be added and the temperature can be elevated to about –50° C. to room temperature.

On the other hand, for example, starting materials of formulae (Va) and (Vb), wherein $R^1$ is methyl, can be prepared by bromination at the para position of a known or commercially available anisole compound according to known methods (e.g., *J. Org. Chem.,* Vol. 58, pp. 7507–, 1993, and *J. Org. Chem.,* Vol. 46, pp. 118–, 1981).

Alternatively, other methods of preparing compounds of formula VI are found in co-pending application U.S. Ser. No. 60/160226, filed Oct. 18, 1999, hereby incorporated by reference in its entirety.

Unless indicated otherwise, the pressure of each of the above reactions is not critical. Generally, the reactions will be conducted at a pressure of about one to about three atmospheres, preferably at ambient pressure (about one atmosphere).

The compounds of formula (VI) and the intermediates shown in the above reaction schemes can be isolated and purified by conventional procedures, such as recrystallization or chromatographic separation.

As indicated above, compounds of the formula (I) can be prepared by biotransformation of the prepared by biotransformation (VI), of which they are metabolites.

A biotransformation can be achieved by those skilled in the art by contacting the substance to be transformed, and other necessary reactants, with the enzymes derived from a variety of living organisms under conditions suitable for a chemical interaction to occur. Subsequently, the products of the reaction are separated and those of interest are purified for elucidation of their chemical structure and physical and biological properties. The enzymes can be present as purified reagents, be in crude extracts or lysates, or be in intact cells and can be in solution, be in suspension (e.g., intact cells), be covalently attached to a supporting surface, or be imbedded in a permeable matrix (e.g., agarose or alginate beads). The substrate and other necessary reactants (e.g., water, air) are supplied as the chemistry dictates. Generally, the reaction is carried out in the presence of one or more liquid phases, aqueous and/or organic, to promote mass transfer of the reactants and products. The reaction can be conducted aseptically or not. The conditions for monitoring the progress of the reaction and the isolation of the products of the reaction will vary according to the physical properties of the reaction system and the chemistry of the reactants and products.

The following is one example of a laboratory-scale method for carrying out an aerobic biotransformation that can be exercised by those skilled in the art to produce compounds of interest. Nutrient medium (e.g., IOWA Medium: dextrose, yeast extract, dipotassium hydrogen phosphate, sodium chloride, soybean flour, water; adjusted to neutral pH) is added to one or more culture vessels (e.g., fermentation tubes or flasks) which are then steam-sterilized. Each vessel is aseptically inoculated with growth from an agar culture, a suspension of washed cells or spores, or broth from a liquid nutrient medium culture of the biotransforming microorganism. The vessels are mounted on a shaker designed for fermentation and shaken (e.g., rotary operation at 100–300 rpm) at an appropriate temperature (e.g., 20–40° C.) long enough to promote the growth of the microorganism to a suitable population size (e.g., 1–3 days).

The parent compound to be transformed (i.e., substrate) is dissolved in water or a suitable water-miscible solvent (e.g., dimethylsulfoxide, dimethylformamide, ethyl alcohol, methyl alcohol). To each of the biotransformation vessels, the resulting solution is aseptically added to achieve the desired concentration of substrate (e.g., 100–200 mcg/mL). The dosed vessels are mounted on the shaker and shaken as before, until the substrate has been converted to product[s] by microbial metabolism (e.g., 1–10 days). The contents of the biotransformation vessel are mechanically treated (e.g., by filtration or centrifugation) to separate undissolved solids from the aqueous phase. The separated solids are extracted with a suitable water-miscible organic solvent (e.g., methanol).

The solvent extract of the solids and the aqueous phase content from the vessels are recovered, combined, and concentrated using suitable methods, e.g., solid phase extraction and drying under reduced pressure. The dried crude is redissolved in a solvent that is compatible with the purification method (e.g., acetonitrile, methanol, water, or HPLC mobile phase). Isolation and purification of the biotransformation product[s] are achieved by solid phase extraction (SPE) followed by reversed phase high performance liquid chromatography (HPLC). The biotransformation produce[s] is monitored during chromatographic separation by UV-absorbance and photodiode array spectral profile. Fractions of the HPLC mobile phase containing the product[s] of interest are retained and the product[s] is extracted from the mobile using suitable methods, e.g., vacuum drying followed by SPE. The solvent eluate from SPE extraction is recovered, filtered to remove solids, and concentrated under reduced pressure to produce dried purified biotransformation product[s]. The chemical structure of the isolated product[s] is determined from the data derived from mass spectroscopy and ¹H-NMR.

As the piperidinylaminomethyl trifluoromethyl cyclic ether compounds of this invention possess at least two asymmetric centers, they are capable of occurring in various stereoisomeric forms or configurations (e.g., diastereoisomers including epimers). Hence, the compounds can exist in separated (+)- and (−)-optically active forms, as well as mixtures thereof. The present invention includes all such forms within its scope. All optical isomers and stereoisomers of the compounds of formula (I) and mixture thereof, are considered to be within the scope of the invention. With respect to the compounds of formula (I), (VI) and (II), the invention includes the use of racemate, one or more enantiomeric forms, one or more diastereomeric forms, or mixture thereof. The compounds of formula (I), (VI) and (II) may also exist as tautomers. This invention relates to use of all such tautomers and mixtures thereof. Individual isomers can be obtained by known methods, such as optical resolution, fractional crystallization, chromatography or H.P.L.C. of a diastereomeric mixture of an intermediate, or a compound of formula (I) or a suitable salt thereof. Also, the individual stereoisomers can be synthesized from the appropriate optically active starting materials or intermediates using any of the general processes described herein. Additionally, methods of preparing enriched diastereomeric mixtures or specific enantiomeric forms are found in co-pending application U.S. Ser. No. 60/160226, filed Oct. 18, 1999, hereby incorporated by reference in its entirety.

In so far as the piperidinylaminomethyl trifluoromethyl cyclic ether compounds of this invention are basic compounds, they are all capable of forming a wide variety of different salts with various inorganic and organic acids. Although such salts must be pharmaceutically acceptable for administration to animals, it is often desirable in practice to initially isolate the base compound of this invention from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate) salts).

The 1-trifluoromethyl-4-hydroxy-7-piperidinylaminomethylchroman derivatives of the present invention, and their pharmaceutically acceptable salts, exhibit significant substance P receptor-binding activity and therefore are of value in the treatment of a wide variety of clinical conditions which are characterized by the presence of an excess of said substance P activity. Such conditions include dysthymia, major depressive disorder, pediatric depression, generalized anxiety disorder, obsessive-compulsive disorder, panic disorder, phobias such as social phobia and agoraphobia; post traumatic stress disorder, borderline personality disorder, acute pain, chronic pain, migraine, angiogenesis, sunburn, urinary incontinence, inflammatory disorders such as rheumatoid arthritis, osteoarthritis, psoriasis, asthma and allergic disorders; emesis, including acute, delayed and anticipatory emesis wherein the emetic agent or condition is chemotherapy, radiation, surgery, motion, migraine or any other emetic agent or condition; disorders caused by *Helicobacter pylori*, cardiovascular disorders, ophthalmic disorders, inflammation of the urinary tract, psychosis, schizophrenia, conduct disorder, disruptive behavior disorder, bipolar disorder, movement disorders such as Tourette's syndrome, akinetic-rigid syndrome, movement disorders associated with Parkinson's disease, tardive dyskinesia and other dyskinesias; cognitive disorders such as dementia (including age related dementia and senile dementia of the Alzheimer's type) and memory disorders (e.g., amnestic disorders), eating disorders such as anorexia nervosa and bulimia nervosa, attention deficit hyperactivity disorder, chronic fatigue syndrome, premature ejaculation, premenstrual syndrome, premenstrual dysphoric disorder, chemical dependencies and addictions, stress related somatic disorders, neuralgia, peripheral neuropathy, gastroesophageal reflux disease, reflex sympathetic dystrophy such as shoulder/hand syndrome; hypersensitivity disorders such as to poison ivy; fibromyalgia, angina, Reynaud's disease, rheumatic diseases such as fibrositis; eczema, rhinitis, allergies, post-herpetia neuralgia, cystitis, inflammatory bowel disease, irritable bowel syndrome, colitis, fibrosing and collagen disorders such as scleroderma and eosinophilic fascioliasis; blood flow disorders due to vasodilatation, and disorders related to immune enhancement or suppression such as systemic lupus erythematosus in a mammal, especially humans. For treatment of emesis, these compounds may preferably be used in combination with a $5HT_3$ receptor antagonist such as ondansetron, granisetron or tropisetron.

The 1-trifluoromethyl-4-hydroxy-7-piperidinylaminomethylchroman derivatives of this invention, and their pharmaceutically acceptable salts, can be administered via either the oral, parenteral (e.g., intravenously, intramuscularly or subcutaneously) or topical routes to mammals. In general, these compounds are most desirably administered to humans in doses ranging from about 0.3 mg up to 750 mg per day, although variations will necessarily occur depending upon the weight and condition of the subject being treated and the particular route of administration chosen. However, a dosage level that is in the range of from about 0.06 mg to about 6 mg per kg of body weight per day is most desirably employed.

Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The 1-trifluoromethyl-4-hydroxy-7-piperidinylaminomethylchroman derivatives of this invention, and their pharmaceutically acceptable salts, may be administered alone or in combination with pharmaceutically acceptable carriers or diluents by any of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the compounds of the present invention topically when treating, for example, inflammatory conditions of the skin and this may preferably be done by way of creams, jellies, gels, pastes, ointments and the like, in accordance with standard pharmaceutical practice.

The activity of the compounds of the present invention, as substance P antagonists, can be determined by their ability to inhibit the binding of substance P at its receptor sites in CHO-cells which express NK1 receptor or IM-9 cells employing radioactive reagents. The substance P antagonist activity of the herein described piperidinylaminomethyl trifluoromethyl cyclic ether compounds can be evaluated by using the standard assay procedure described by D. G. Payan et al., (J. Immunology, Vol. 133, p. 3260, 1984). This method essentially involves determining the concentration of the individual compound required to reduce by 50% the amount of radiolabeled substance P (SP) reagents at their receptor sites in said isolated cow tissues or IM-9 cells, thereby affording characteristic $IC_{50}$ values for each compound tested. More specifically, inhibition of [$^3$H]SP binding to human IM-9 cells by compounds are determined in assay buffer (50 mM Tris-HCl (pH 7.4), 1 mM $MnCl_2$, 0.02% bovine serum albumin, bacitracin (40 µg/ml), leupeptin (4 µg/ml), chymostatin (2 µg/ml) and phosphoramidon (30 µg/ml)). The reaction is initiated by the addition of cells to assay buffer containing 0.56 nM [$^3$H]SP and various concentrations of compounds (total volume; 0.5 ml) and incubation for 120 min at 4° C. Incubation is terminated by filtration onto GF/B filters (presoaked in 0.1% polyethylenimine for 2 hours). Nonspecific binding is defined as the radioactivity remaining in the presence of 1 mM SP. The filters are placed into tubes and counted using a liquid scintillation counter.

Alternatively, the anti-inflammatory activity of the compounds of this invention, in the periphery of a mammalian subject, is demonstrated by a capsaicin-induced plasma extravasation test, using the procedure described by A. Nagahisa et al, (European Journal of Pharmacology, Vol. 217, pp. 191–195, 1992). In this test, anti-inflammatory activity is determined as the percent inhibition of plasma protein extravasation in the ureter of pentobarbital-anesthetized (25 mg/kg i.p.) male Hartley guinea pigs (weighing 300–350 g). Plasma extravasation is induced by intraperitoneal injection of capsaicin (30 mM in 0.1 BSA containing buffer, 10 ml/animal) into the animals, which are fasted overnight. The compounds of this invention were dissolved in 0.1% methyl cellulose-water and given orally 1 hour before capsaicin challenge. Evans blue dye (30 mg/kg) was administered intravenously 5 minutes before challenge. The animals were killed 10 minutes after capsaicin injection and both right and left ureter were removed. Tissue dye content was quantitated at 600 nm absorbance after overnight formamide extraction.

The compound prepared in Example 3 of this invention showed 98% inhibition at 0.03 mg/kg, while the structurally closest compound in Example 18 of WO 97/08114 showed 72% at the same dosage.

The adverse effect on $Ca^{2+}$ channel binding affinity is determined by study of verapamil binding in a rat heart membrane preparation. More specifically, verapamil binding is performed as previously described by Reynolds et al., (J. Pharmacol. Exp. Ther. Vol. 237, p. 731, 1986). Briefly, incubations are initiated by the addition of tissue to tubes containing 0.25 nM [$^3$H]desmethoxyverapamil and various concentrations of compounds (total volume 1 ml). Nonspecific binding is defined as radioligand binding remaining in the presence of 3–10 µM methoxyverapamil.

The activity of the compounds of this invention against CNS disorders is determined in a [$Sar^9$, $Met(O_2)^{11}$] substance P-induced tapping test in gerbils using a modification of the method of N. M. J. Rupniak (European Journal of Pharmacology, Vol. 265, pp. 179–183, 1994) and L. J. Bristow (European Journal of Pharmacology, Vol. 253, pp. 245–252, 1994). More specifically, first a compound of this invention is subcutaneously administered into a gerbil. Second, gerbils are lightly anesthetized with ether and the skull surface is exposed. Third, [$Sar^9$, $Met(O_2)^{11}$]substance P (5 µl) are administered directly into the lateral ventricles via a 25 gauge needle inserted 3.5 mm below lambda. Then, gerbils are placed individually in 1 liter beakers and monitored for repetitive hind paw tapping.

Anti-emetic activity of the compounds of this invention can be demonstrated in cisplatin-induced emesis test in ferrets. A compound of this invention is subcutaneously administered to the ferrets (male, b.w.=1.3–1.6 kg) 30 minutes before cisplatin injections. Cisplatin is intraperitoneally injected to the ferrets, and their emetic episodes (i.e., retching, vomiting and gagging) are recorded by a video camera for 4 hours. The frequencies of the episodes are counted.

The susceptibility to metabolism of the compounds of this invention can be evaluated by an in-vitro assay that comprises (a) contacting a sample compound with a reagent composition prepared by adding a specific cytochrome P-450 (e.g., CYP2D6) isozyme to poor metabolizer (abbreviated as PM) liver microsomes (i.e., liver microsomes of a human lacking said specific cytochrome P-450 isozyme) in a carrier material, and (b) analyzing the substrate by a mass spectrometer linked with a HPLC (high performance liquid chromatography). More specifically, the substrate (1 $\mu$M) is incubated with PM human liver microsome (manufactured by Keystone Skin Bank) supplemented with a recombinant CYP2D6-expressing microsome (0–0.1 mg/ml) or control vector microsomes in the presence of 1.3 mM NADP (nicotinamide adenine dinucleotide phosphate), 0.9 mM NADH (reduced nicotinamido adenine dinucleotide), 3.3 mM $MgCl_2$ and 8 units/ml G-6-PDH (glucose-6-phosphate dehydrogenase) respectively in a total volume of 1.2 ml of 100 mM potassium phosphate buffer. The pH of the solution is 7.4, and the incubation temperature is $37_iC$. At specific incubation times (0, 5, 10, 30 and 60 minutes), an aliquot of 100 $\mu$l is withdrawn from the reaction mixture and mixed with 1 ml of acetonitrile (ACN) containing 5 ng/ml (2S,3S)-3-(2-methoxybenzylamino)-2-diphenylmethyl-1-azabicyclo[2.2.2]octane as an internal standard (prepared according to the procedures disclosed in WO 90/05729). Protein is subsequently precipitated by centrifugation (1,800×g for 10 min), and the resulting supernatant is taken. Concentration of substrates and products in the sample solutions are analyzed with a Sciex API-III mass spectrometer linked with a Hewlett-Packard HP1090 HPLC system. Concentrations of the remaining substrates in each sample solution (%-remaining) are plotted against the desired incubation times. The values of $T_{1/2}$ are obtained in each graph. The ratios of the $T_{1/2}$ values of the compound tested are calculated (i.e., $T_{1/2}$ ratio=($T_{1/2}$ by control vector microsome)/($T_{1/12}$ by PM human liver microsome supplemented CYP2D6-expressing microsome)).

EXAMPLES

The present invention is illustrated by the following examples. However, it should be understood that the invention is not limited to the specific details of these examples. Melting points (mp) were taken with a Buchi micro melting point apparatus and not corrected. Infrared absorption spectra (IR) were measured by a Shimadzu infrared spectrometer (IR-470). $^1$H nuclear magnetic resonance spectra (NMR) was measured in $CDCl_3$ by a JEOL NMR spectrometer (JNM-GX270, 270 MHz for $^1$H) unless otherwise indicated and peak positions are expressed in parts per million (ppm) downfield from tetramethylsilane. The peak shapes are denoted as follows: s, singlet; d, doublet; t, triplet; m, multiplet.

Example 1

Preparation of (2S,3S)-3-(6-Methoxy-1-methyl-1-trifluoromethylisochroman-7-yl)methylamino-2-phenylpiperidine dihydrochloride (i) 2-(2-Bromo-5-methoxyphenyl)ethanol To a stirred mixture of 3-methoxyphenethyl alcohol (1.18 g, 7.8 mmol) and pyridine (0.75 ml, 9.3 mmol) in dry dichloromethane (10 ml) was added bromine (0.47 ml, 18.0 mmol) dropwise under nitrogen at 0° C. The orange solution was stirred at room temperature for 4 hours (hr). The reaction mixture was quenched by the addition of 10% sodium bisulfite aqueous solution., and extracted with dichloromethane. The organic extracts were washed with brine, dried over magnesium sulfate, and concentrated to give crude products, which were purified by silica-gel column chromatography eluted with gradient of hexane and ethyl acetate (10:1, 8:1, 5:1) to give the title compound as a colorless oil (1.5 g, 83.2%). $^1$H-NMR ($CDCl_3$): 7.43 (d, J=8.8 Hz, 1H), 6.83 (d, J=3.3 Hz, 1H), 6.67 (dd, J=8,8, 3.3 Hz, 1H), 3.91–3.81 (m, 2H), 3.78 (s, 3H), 2.99 (t, J=6.6 Hz, 2H).

(ii) 2-(2-(2-Bromo-5-methoxyphenyl)ethoxy)tetrahydropyran

To a stirred mixture of 2-(2-bromo-5-methoxyphenyl)ethanol (1.5 g, 6.5 mmol) and dihydropyran (13.0 mmol) in dry dichloromethane (30 ml) was added camphor sulfonic acid (0.3 mmol) under nitrogen at 0° C. for 1 hour. The reaction mixture was quenched with saturated sodium bicarbonate solution, and extracted with dichloromethane. The organic extracts were washed with brine, dried over magnesium sulfate, and concentrated to give a crude product. This was purified by silica-gel column chromatography eluted with a mixed solvent of hexane and ethyl acetate (20:1) to give the title compound (2.05 g, quantitative). $^1$H-NMR ($CDCl_3$): 7.40 (d, J=8.8 Hz, 1H), 6.86 (d, J=2.9 Hz, 1H), 6.65 (dd, J=8.8, 2.9 Hz, 1H), 4.63–4.60 (m, 1H), 3.99–3.90 (m, 1H), 3.82–3.74 (m, 1H), 3.78 (s, 3H), 3.68–3.59 (m, 1H), 3.50–3.45 (m, 1H), 3.02 (t, J=7.0 Hz, 2H), 1.83–1.52 (m, 6H).

(iii) 1,1,1-Trifluoro-2-(4-methoxy-2-(2-(tetrahydropyran-2-yloxy)ethyl)phenyl)-propan-2-ol To a stirred solution of 2-(2-(2-bromo-5-methoxyphenyl)-ethoxy)tetrahydropyran (1.0 g, 3.17 mmol) in dry tetrahydrofuran (20 ml) was added n-butyllithium (2.5 ml, 4.12 mmol) dropwise under nitrogen at −78° C. The reaction mixture was stirred at −40° C. for 1 hr. To the reaction mixture was added a suspension of anhydrous cerium chloride (884 mg, 3.58 mmol) in dry tetrahydrofuran (15 ml) dropwise at −78° C. and stirred for 1 hr. To the reaction mixture was added trifluoroacetone (0.5 ml, 5.59 mmol), and the resulting mixture was stirred at −78° C. for 1 hr. This was quenched by saturated ammonium chloride solution, extracted with dichloromethane. The combined organic extracts were dried over magnesium sulfate, and concentrated to give a crude products, which were purified by silica-gel column chromatography eluted with a gradient of hexane and ethyl acetate (20:1, 15:1, 12:1, 10:1) to give the title compound (555 mg, 50.3%). $^1$H-NMR($CDCl_3$): 7.35–7.31 (m, 1H), 6.78–6.74 (m, 2H), 5.70 and 5.62 (each s, total 1H), 4.63 and 4.48 (each m, total 1H), 4.18–4.11 and 3.99–3.92 (each m, total 1H), 3.80 (s, 3H), 3.77–3.43 (m, 3H), 3.33–2.90 (m, 2H), 1.80 and 1.78 (each s, total 3H), 1.75–1.26 (m, 6H).

(iv) 6-Methoxy-1-methyl-1-trifluoromethylisochroman

A mixture of 1,1,1-Trifluoro-2-(4-methoxy-2-(2-(tetrahydropyran-2-yloxy)ethyl)phenyl)propan-2-ol (470 mg, 1.35 mmol) and conc. hydrochloric acid (4 ml) was stirred at 120° C. for 3 hr. After cooling, the reaction mixture was diluted with water, and the aqueous layer was extracted with dichloromethane. The organic extracts were dried over magnesium sulfate, and concentrated to give the title compound as a brown oil (460 mg). This was used without further purification.

(v) 6-Methoxy-1-methyl-1-trifluoromethylisochroman-7-carbaldehyde

To a stirred solution of 6-methoxy-1-methyl-1trifluoromethylisochroman (460 mg) in dry dichloromethane (5 ml) was added titanium(IV) chloride under nitrogen at −78° C. After 15 minutes, to the yellow solution was added a solution of dichloromethyl methyl ether in dry dichloromethane at the same temperature. The reaction mixture was stirred at −78° C. for one hour, poured onto ice water, and stirred at room temperature for 30 minutes. The aqueous layer was extracted with methylene chloride. The extracts were washed with brine, dried over magnesium sulfate, and concentrated to give a crude product. This was purified by silica-gel column chromatography eluted with a gradient of hexane and ethyl acetate (10:1, 8:1, 6:1) to give the title compound (179 mg, 48.3% from 1,1,1-Trifluoro-2-(4-methoxy-2-(2-(tetrahydropyran-2-yloxy)ethyl)phenyl)-propan-2-ol). $^1$H-NMR(CDCl$_3$): 10.41 (s, 1H), 7.82 (s, 1H), 6.78 (s, 1H), 4.19–4.11 (m, 1H), 3.94 (s, 3H), 3.94–3.87 (m, 1H), 2.91 (t, J=4.4 Hz, 2H), 1.67 (s, 3H).

(vi) 1-tert-Butoxycarbonyl-(2S,3S)-3-(6-methoxy-1-methyl-1-trifluoromethylisochroman-7-yl)methylamino-2-phenylpiperidine To a stirred solution of 1-tert-butoxycarbonyl-(2S,3S3-amino-2-phenylpiperidine (0.67 mmol) which was prepared by a method described in WO 97/03066 and 6-methoxy-1-methyl-1-trifluoromethylisochroman-7-carbaldehyde (184 mg, 0.67 mmol) in dry dichloromethane (3 ml) was added a molar excess of sodium triacetoxyborohydride portion-wise under nitrogen at room temperature. The reaction mixture was stirred at room temperature for five hours. The mixture was then made basic via the addition of saturated sodium bicarbonate solution, extracted with dichloromethane, dried over magnesium sulfate, and concentrated to give a crude product. This was purified by silica-gel column chromatography eluted with a gradient of dichloromethane and methanol (50:1, 25:1, 20:1) to give the title compound (330 mg, 91.8%). $^1$H-NMR(CDCl$_3$): 7.59–7.55 (m, 2H), 7.34–7.17 (m, 4H), 6.56 (s, 1H), 5.44 (m, 1H), 4.16–4.08 (m, 1H), 3.99–3.84 (m, 2H) 3.80 (m, 2H), 3.72 and 3.71 (each s, total 3H), 3.06–2.98 (m, 2H), 2.83–2.81 (m, 2H), 1.85–1.61 (m, 4H), 1.63 and 1.61 (each s, total 3H), 1.50–1.40 (m, 1H), 1.39 (s, 9H).

(vii) (2S,3S)-3-(6-Methoxy-1-methyl-1-trifluoromethylisochroman-7-yl)methylamino-2-phenylpiperidine dihydrochloride To a stirred solution of 1-tert-butoxycarbonyl-(2S,3S)-3-(6-methoxy-1-methyl-1-trifluoromethylisochroman-7-yl) methylamino-2-phenylpiperidine (325 mg, 0.61 mmol) in ethyl acetate (5 ml) was added a methanolic HCl solution dropwise under nitrogen at room temperature for 8 hours. The solvent was removed, and recrystallized from ethanol to give the title compound (88 mg, 28.4%). mp: 193–201° C. $^1$H-NMR (major isomer, free amine, CDCl$_3$): 7.33–7.20 (m, 5H), 6.95 (s, 1H), 6.43 (s, 1 H), 4.13–4.09 (m, 1H), 3.92–3.84 (m, 2H), 3.62 (d, J=13.9 Hz, 1H), 3.51 (s, 3H), 3.33 (d, J=13.9 Hz, 1H), 3.31–3.24 (m, 1H), 2.84–2.74 (m, 4H), 2.12–2.07 (m, 1H), 1.94–1.82 (m, 1H), 1.67–1.62 (m, 1H), 1.59 (s, 3H), 1.43–1.38 (m, 1H)

The diastereomeric ratio of epimers at the 1-position on the isochroman ring was determined by $^1$H-NMR as 5:1 (1R:1S). These isomers are (2S,3S)-3-[(1R)-6-methoxy-1-methyl-1-trifluoromethylisochroman-7-yl]methylamino-2-phenylpiperidine and (2S,3S)-3-[(1S)-6-methoxy-1-methyl-1-trifluoromethylisochroman-7-yl]methylamino-2-phenylpiperidine. The more soluble epimer was recovered from the mother liquor. The diastereomeric ratio of epimers at the 1-position on the isochroman ring was determined by $^1$H-NMR as 1:3 (1R:1S). The absolute stereochemistry of the title compounds were determined by X-ray crystallography of the (3R) isomer after further purification by recrystallization. $^1$H-NMR (major isomer, free amine, CDCl$_3$): 7.33–7.20 (m, 5H), 6.99 (s, 1H), 6.40 (s, 1H), 4.13–4.09 (m, 1H), 3.92–3.84 (m, 2H), 3.62 (d, J=13.9 Hz, 1H), 3.45 (s, 3H), 3.33 (d, J=13.9 Hz, 1H), 3.31–3.24 (m, 1H), 2.84–2.74 (m, 4H), 2.12–2.07 (m, 1H), 1.94–1.82 (m, 1H), 1.67–1.62 (m, 1H), 1.59 (s, 3H), 1.43–1.38 (m, 1H).

Example 2

(2S,3S)3-[(1R)-6-Methoxy-1 -methyl-1-trifluoromethylisochroman-7-yl]-methylamino-2-phenylpiperidine dihydrochloride (i) 6-Hydroxy-1-methyl-1-trifluoromethylisochroman To a stirred solution of 6-Methoxy-1-methyl-1-trifluoromethylisochroman (71 g, 0.29 mol) in acetic acid (600 mL) was added aqueous 48% HBr (300 mL) and the mixture was stirred at 130° C. for 13 hr. After removing acetic acid in vacuo, the reaction mixture was treated with aqueous NaOH (8 M) until the pH became 5–6. The resultant solution was extracted with ethyl acetate (400 mL×2) and the combined ethyl acetate extracts were washed with brine (100 mL), dried over MgSO$_4$, and concentrated in vacuo. Flash chromatography (Silica-gel, 15×20 cm, 17% ethyl acetate/hexane) afforded 6-hydroxy-1-methyl-1-trifluoromethylisochroman (67 g, 100%) as a colorless oil. $^1$H-NMR(CDCl$_3$): 7.22 (d, J=9.1 Hz, 1H), 6.73 (dd, J=9.1, 2.6 Hz, 1H), 6.63 (d, J=2.6 Hz, 1H), 5.00 (s, 1H, 4.17–4.07 (m, 1H), 3.90 (dt, J=11, 5.8 Hz, 1H), 2.84–2.78 (m, 2H), 1.64 (s, 3H).

(ii) 6-Acetoxy-1-methyl-1-trifluoromethylisochroman

To a stirred solution of 6-hydroxy-1-methyl-1-trifluoromethylisochroman (79 g, 0.34 mol) and triethylamine (120 mL, 0.88 mol) in THF (680 mL) was added acetyl chloride (31 mL, 0.44 mol) at 0° C., and the mixture was stirred at room temperature for 1 hr. The reaction was quenched by adding aqueous 1 N-HCl (400 mL), and extracted with ethyl acetate (500 mL). The extracts were washed with aqueous saturated NaHCO$_3$ (100 mL) and brine (100 mL), dried over MgSO$_4$, and concentrated in vacuo. The residue was purified by flash chromatography (Silica-gel, 15×20 cm, 6% ethyl acetate/hexane) to afford 6-acetoxy-1-methyl-1-trifluoromethylisochroman (83 g, 89%) as a colorless oil. $^1$H-NMR(CDCl$_3$): 7.36 (d, J=7.2 Hz, 1H), 6.98 (dd, J=7.2, 2.5 Hz, 1H), 6.91 (d, J=2.5 Hz, 1H), 4.18–4.08 (m, 1H), 3.92 (dt, J=11, 5.4 Hz, 1H), 2.86 (t, J=5.4 Hz, 2H), 2.30 (s, 1H), 1.66 (s, 3H).

(iii) (1R)-6-Acetoxy-1-methyl-1-trifluoromethyl-isochroman and (1S)-Hydroxy-1-methyl-1-trifluoromethyl-isochroman A mixture of racemic 6-acetoxy-1-methyl-1-trifluoromethylisochroman (38.4 g, 0.140 mol), 10% sec-butanol solution in hexane (1.3 L), and lipase PS (35 g) was stirred vigorously at room temperature for 23 hr. After filtration, the filtrate was concentrated under reduced pressure to give a mixture. This was purified by silica-gel column chromatography eluted with gradient of hexane and ethyl acetate (15:1,5:1,2:1) to give, first, (1R)6-acetoxy-1-methyl-1-trifluoromethyl-isochroman as a colorless oil (17.3 g, 45%, 94%ee). The $^1$H-NMR spectra of this compound was identical with that of racemate. The second fraction gave (1S)-4-hydroxy-1-methyl-1-trifluoromethylisochroman as crystals (16.9 g, 52%, 83%ee). The $^1$H-NMR spectra of this material was identical with that of racemate.

(iv) (1R)-Hydroxy-1-methyl-1-trifluoromethyl-isochroman

To a stirred mixture of (1R)-6-acetoxy-1-methyl-tifluoromethyl-isochroman (35.5 g, 0.129 mol), methanol (860 mL), and water (340) was added potassium carbonate (35.7 g, 0.258 mol) at 0° C., then the mixture was stirred at room temperature for 1 hr. The resultant mixture was acidified with 2 N hydrochloric acid (pH 3) and evaporated in vacuo to remove methanol. The residue was extracted with ethyl acetate. The organic layer was washed with water and brine, and dried over magnesium sulfate. After filtration, the filtrate was concentrated under reduced pressure to afford the title compound as a colorless oil (28.0 g, 93%). This was used without further purification. The $^1$H-NMR spectra of this compound was identical with that of the racemate.

(v) (1R)-Methoxy-1-methyl-1-trifluoromethyl-isochroman

To a stirred mixture of sodium hydride (3.47 g, 0.145 mol) in DMF (50 mL) was added (1R)-hydroxy-1-methyl-1-trifluoromethylisochroman (28.0 g, 0.121 mol) solution in DMF (370 mL) at 0° C., then the mixture was stirred at room temperature for 1 hr. The reaction mixture was quenched with water and diluted with saturated aqueous ammonium chloride. This was extracted with ethyl acetate-toluene (4:1). The organic fraction was washed with water and brine, and dried over magnesium sulfate. The solvent was removed in vacuo, the residue was purified by column chromatography on silica-gel eluted with hexane and ethyl acetate (40:1) to give the title compound as a colorless oil (29.1 g, 98%). The $^1$H-NMR spectra of this material was identical with that of racemate.

(vi)(2S,3S)-3-[(1R)-Methoxy-1-methyl-1-trifluoromethyl-7-yl]methylamino-2-phenylpiperidine dihydrochloride The above (1R)-Methoxy-1-methyl-1-trifluoromethyl-isochroman was further converted to the title compound by following the method for preparation of Example 3 to afford the title compound in a single diastereomeric form. Optical Rotation: $[\alpha]^{27}_D$=+75.44$_i$ (c=0.424, MeOH).

Example 3 (Microbial Biotransformation)

6-Methoxy-1-methyl-7-[(2-phenyl-piperidin-3-ylamino)-methyl]-1-trifluoromethyl-isochroman-4-ol Twenty-five mL of IOWA Medium (anhydrous dextrose, 20 g; yeast extract, 5 g; dipotassium hydrogen phosphate, 5 g; sodium chloride, 5 g; soybean flour, 5 g; distilled water, 1 L; adjusted to pH 7.2 with 1N sulfuric acid) were added to each of eighteen 125-mL Delong flasks with Morton closures and the resulting combinations were steam-sterilized for 30 minutes at 15 psig and 121° C. Two flasks (inoculum stage) were aseptically inoculated with 0.25 mL of a cryogenically stored (−80° C.) axenic stock of *Streptomyces punipalus* (NRRL 3529) mycelium. The inoculated flasks were mounted vertically on a rotary shaker (2-inch throw) and shaken at 210 rpm and 29° C. for 2 days. Then, 2.5 mL of broth from the inoculum stage was aseptically transferred to the remaining 15 flasks (biotransformation stage). The inoculated biotransformation flasks were mounted vertically on a rotary shaker (2-inch throw) and shaken at 210 rpm and 29° C. for 1 day. The dihydrochloride salt of (6-methoxy-1-methyl-1-trifluoromethyl-isochroman-7-ylmethyl)-2-phenyl-piperidin-3-yl)-amine (i.e., substrate) was dissolved in distilled water (6.5 mg/mL). To each of the 15 biotransformation flasks, 0.75 mL of the resulting solution was aseptically added to give an initial substrate concentration of 173 mcg/mL (73.1 mg total in 15 flasks). The dosed flasks were remounted vertically on the rotary shaker and shaken at 210 rpm and 29° C. for an additional 4 days. The progress of the formation of the biotransformation product was monitored by reverse phase HPLC analysis of daily 1-mL samples. At the end of the 4-day biotransformation period, 25 mL of methanol was added to each flask and mixed with the contents (i.e., broth). The resultant broth/methanol mix from all 15 flasks was pooled. The flasks were then rinsed sequentially twice, once with 50 mL methanol and again with 25 mL methanol. The rinses were pooled with the earlier extract to give a total volume of about 775 mL. This broth/methanol pool was centrifuged (RC5B centrifuge, 6000 rpm, 8 min.) to remove solids. The supernatant (A) was retained. The solids were resuspended in 100 mL methanol, mixed, and centrifuged as before. The supernatant (B) was combined with the retained earlier supernatant (A) and filtered by vacuum through a glass fiber (Whatman GF/B) filter. Subsequently, the filtrate was subjected to distillation under reduced pressure at 45° C. to remove methanol. The resultant ~300 mL of aqueous heel was applied under pressure of nitrogen gas (30 psig) to a prepared C18 resin cartridge (Biotage KP-C18-WP, 20–40 $\mu$M) for the purpose of solid phase extraction (SPE). [The cartridge was prepared for loading of compound by washing first with 1250 mL methanol and second by washing with 2250 mL of distilled water.] After loading, the column was washed with 2050 distilled water to remove unbound material. The loaded column was washed with 975 mL of a 50% methanol solution (1:1 MeOH/H$_2$O) to remove unwanted material. The compound of interest was eluted with 975 mL of methanol. The eluate was subjected to distillation under reduced pressure at 45° C. to remove methanol. The material remaining after the removal of methanol was dissolved in a 20% methanol in water solution and loaded by vacuum onto a C18 resin cartridge (Waters Sep-Pak 6 cc (1 g) C18) for SPE. [The cartridge was prepared for loading by washing first with 15 mL methanol and second by washing with 15 mL distilled water.] The loaded SPE cartridge was purged of unbound compounds with 20 mL of a 20% methanol in water solution. Compounds bound to the resin were eluted with 10 mL volumes of methanol in water solutions of increasing solvent strength (50, 55, 60, 65, 70, 75, 80, 85, 90, 95, 100%). Almost all of the compound of interest eluted from the SPE cartridge in the 60–70% methanol eluates (trace in 55% eluate). The eluents containing the title compound were pooled and taken to dryness at 45° C. by a stream of nitrogen gas. During drying, anhydrous ethanol was added as required to drive off water. The dried crude weighed 59 mg. It was dissolved in a 75% methanol in water and subjected to reversed phase high performance liquid chromatography (HPLC Method 1) to isolate the title compound.

| HPLC Method 1 | |
|---|---|
| Column: | Luna 5 μ C18(2), 21.2 × 250 mm. |
| Mobile phase: | linear gradient from 2–30 min.; (20–80)% acetonitrile : (80–20)% aqueous buffer [95% 20 mM ammonium acetate, unadjusted pH 6.8 / 5% MeOH]. |
| Flow rate: | 9 mL/min. |
| Monitor: | UV absorbance at 281 nm; photodiode array at 200–400 nm (4.8 nm slit). |
| Run Time: | 30 min. |

The title compound had a retention time of approximately 17.3. Eluting HPLC mobile phase fractions containing the title compound were collected, stripped of solvent (acetonitrile) under vacuum at 45° C., and loaded onto a fresh SPE cartridge (Waters 6 cc C18; preparation as described previously), washed with distilled water to remove salt, and eluted with 10 mL methanol. This eluate was concentrated to dryness under a stream of $N_2$ gas. The dried material was dissolved in 50% methanol/water solution and subjected to reversed phase high performance liquid chromatography (HPLC Method 2) to isolate the title compound.

| HPLC Method 2 | |
|---|---|
| Column: | Luna 5 μ C18(2), 21.2 × 250 mm. |
| Mobile phase: | linear gradient from 2–30 min.; (5–75)% acetonitrile : (95–25)% aqueous buffer [20 mM acetic acid in distilled water, adjusted to pH 4.0 with 1N $H_2SO_4$]. |
| Flow rate: | 9 mL/min. |
| Monitor: | UV absorbance at 281 nm; photodiode array at 200–400 nm (4.8 nm slit). |
| Run Time: | 30 min. |

The title compound had a retention time of approximately 21.8 minutes. Eluting HPLC mobile phase fractions containing the title compound were collected in a vessel containing 20 mL ammonium acetate buffer (HPLC Method 1 aqueous mobile phase). The pool of collected HPLC fractions containing the title compound was stripped of solvent (acetonitrile) under vacuum at 45° C., loaded onto a fresh SPE cartridge (Waters 6 cc C18; preparation as described previously), washed with 20 mL distilled water to remove salts, and eluted with 10 mL methanol. The methanol eluate was stripped of solvent by a stream of nitrogen gas at 45° C. The dried material was dissolved in anhydrous ethanol and taken to dryness under reduced pressure. A total of 19.3 mg of the title compound was obtained. The overall process molar yield was 29.7%

The title compound had a retention time of 13.9 min. in HPLC Method 3. The parent compound had a retention time of 17.5 min. in this method.

| HPLC Method 3 | |
|---|---|
| Column: | Symmetry C18, 3.9 × 150 mm. |
| Mobile phase: | linear gradient from 2–30 min.; (15–90)% acetonitrile : (85–10)% aqueous buffer [20 |

-continued

| HPLC Method 3 | |
|---|---|
| | mM acetic acid in distilled water, adjusted to pH 4.0 with 1 N $H_2SO_4$]. |
| Flow rate: | 1 mL/min. |
| Monitor: | UV absorbance at 281 nm; photodiode array at 200–400 nm (4.8 nm slit). |
| Run Time: | 30 min. |

It had UV-light absorbance maxima at 205 nm, 229 nm (shoulder only), and 280 nm. MS (APCl+): 451.3 (M+H).

Example 4 (Microsomal Biotransformation)

6-methoxy-1-methyl-7-[(2-phenyl-piperidin-3-ylamino)-methyl]-1-trifluoromethyl-isochroman-4-ol An alternative to synthesis by microbial biotransformation (Example 3) can be achieved by using a recombinant cell microsomal reaction mixture. The reaction contains the following components:

| 700 μL | 100 mM potassium phosphate buffer (pH 7.4) | |
|---|---|---|
| 200 μL | cofactor solution | |
| 20 μL | 15 mM parent compound dissolved in distilled water | |
| 80 μL | baculovirus-infected insect cell microsomes co-expressing human P450 (CYP2D6) and human cytochrome P450-NADPH reductase. | |
| 100 mM potassium phosphate buffer | | |
| 8.1 mL | 100 mM $K_2HPO_4$ in distilled water | |
| 1.9 mL | 100 mM $KH_2PO_4$ in distilled water | |
| Cofactor solution | | |
| 4 mg | NADP+ | (e.g., Sigma N-0505) |
| 75 mg | isocitric acid | (e.g., Sigma I-1252) |
| 198 mL | isocitric dehydrogenase | (e.g., Sigma I-2002) |
| 802 mL | 125 mM $MgCl_2$ in distilled water | |

Reaction components were added to a 16×125 mm glass test tube with a stainless steel Morton closure. The tube was incubated on a rotary shaker (1-in. throw) at 240 rpm and 37° C. The progress of the reaction was monitored at 0, 5, and 24 hours after initiation by analysis using reverse phase HPLC (Method 3; described in Example 3). To stop the reaction and prepare the sample for analysis, a 250 mL sample was added to 250 mL methanol, mixed, cooled on ice for 15 min., and centrifuged (Eppendorf microfuge, 14,000 rpm, 5 min.) to remove precipitated proteins. The reaction was complete by 5 hours after initiation. The molar conversion was calculated to be 9.9%. HPLC and APCl+ characteristics of the product were the same as for the title compound in Example 3.

What is claimed is:

1. A compound of the formula (I):

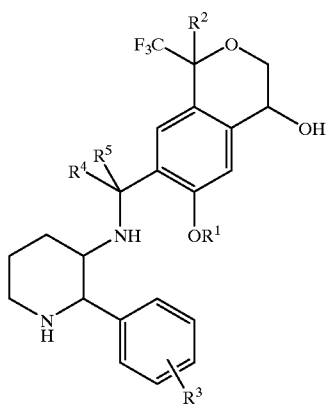

(1)

and its pharmaceutically acceptable salts, wherein $R^1$ is $C_1-C_6$ alkyl;
$R^2$ is hydrogen, $C_1-C_6$ alkyl, halo $C_1-C_6$ alkyl or phenyl;
$R^3$ is hydrogen or halo; and
$R^4$ and $R^5$ are independently hydrogen, $C_1-C_6$ alkyl or halo $C_1-C_6$ alkyl.

2. A compound according to claim 1, wherein
$R^1$ is $C_1-C_3$ alkyl;
$R^2$ is hydrogen, $C_1-C_3$ alkyl, halo $C_1-C_3$ alkyl or phenyl;
$R^3$ is hydrogen or fluorine; and
$R^4$ and $R^5$ are independently hydrogen, $C_1-C_3$ alkyl or halo $C_1-C_3$ alkyl.

3. A compound according to claim 2, wherein $R^1$ is methyl; $R^2$ is hydrogen, methyl, trifluoromethyl or phenyl; $R^3$ is hydrogen; and $R^4$ and $R^5$ are hydrogen.

4. A compound according to claim 1 which is (2S,3S)-3-(6-methoxy-4-hydroxy-1-methyl-1-trifluoromethylisochroman-7-yl)methylamino-2-phenylpiperidine or a pharmaceutically acceptable salt thereof.

5. A pharmaceutical composition for treating a disorder or condition, for which antagonist activity toward substance P is needed, in a mammal, which comprises an amount of the compound of claim 1, or a pharmaceutically acceptable salt thereof, that is effective in treating such disorder or condition, and a pharmaceutically acceptable carrier.

6. A pharmaceutical composition for treating a disorder or condition selected from dysthymia, major depression, pediatric depression, general anxiety, obsessive-compulsive disorder, panic disorder, social phobia, agoraphobia, post traumatic stress, acute pain, chronic pain, migraine, angiogenesis, sunburn, urinary incontinence, inflammatory disorders selected from rheumatoid arthritis, osteoarthritis, psoriasis, asthma and allergies; acute, delayed and anticipatory emesis; disorders caused by *Helicobacter pylori*, cardiovascular disorders, ophthalmic disorders, inflammation of the urinary tract, psychosis, schizophrenia, disruptive behavior disorder, bipolar disorder; movement disorders selected from Tourette's syndrome, akinetic-rigid syndrome, Parkinson's disease, tardive dyskinesia and other dyskinesias; cognitive disorders selected from dementias and memory impairment; eating disorders selected from anorexia nervosa and bulimia nervosa; attention deficit hyperactivity disorder, chronic fatigue syndrome, premature ejaculation, premenstrual syndrome, premenstrual dysphoric disorder, chemical dependencies and addictions, stress related somatic disorders, neuralgia, peripheral neuropathy, gastroesophageal reflux disease, shoulder/hand syndrome of reflex sympathetic dystrophy; poison ivy hypersensitivity; fibromyalgia, angina, Reynaud's disease, fibrositic rheumatic disease, eczema, rhinitis, allergies, post-herpetia neuralgia, cystitis, inflammatory bowel disease, irritable bowel syndrome, colitis; fibrosing and collagen disorders selected from scleroderma and eosinophilic fascioliasis; blood flow disorders due to vasodilatation, and systemic lupus erythematosus in a mammal, comprising an amount of the compound of claim 1, or a pharmaceutically acceptable salt thereof, that is effective in treating such disorder or condition, and a pharmaceutically acceptable carrier.

7. A method of treating a disorder or condition for which antagonist activity toward substance P in needed, in a mammal, which comprises administering to a mammal in need of such prevention or treatment an amount of a compound of claim 1, or a pharmaceutically acceptable salt thereof, that is effective in treating such disorder or condition.

8. A method of treating a disorder or condition selected dysthymia, major depression, pediatric depression, general anxiety, obsessive-compulsive disorder, panic disorder, social phobia, agoraphobia, post traumatic stress, acute pain, chronic pain, migraine, angiogenesis, sunburn, urinary incontinence, inflammatory disorders selected from rheumatoid arthritis, osteoarthritis, psoriasis, asthma and allergies; acute, delayed and anticipatory emesis; disorders caused by *Helicobacter pylori*, cardiovascular disorders, ophthalmic disorders, inflammation of the urinary tract, psychosis, schizophrenia, disruptive behavior disorder, bipolar disorder; movement disorders selected from Tourtte's syndrome, akinetic-rigid syndrome, Parkinson's disease, tardive dyskinesia and other dyskinesias; cognitive disorders selected from dementias and memory impairment; eating disorders selected from anorexia nervosa and bulimia nervosa; attention deficit hyperactivity disorder, chronic fatigue syndrome, premature ejaculation, premenstrual syndrome, premenstrual dysphoric disorder, chemical dependencies and addictions, stress related somatic disorders, neuralgia, peripheral neuropathy, gastroesophageal reflux disease, shoulder/hand syndrome of reflex sympathetic dystrophy; poison ivy hypersensitivity, fibromyalgia, angina, Reynaud's disease, fibrositic rheumatic disease; eczema, rhinitis, allergies, post-herpetia neuralgia, cystitis, inflammatory bowel disease, irritable bowel syndrome, colitis; fibrosing and collagen disorders selected from scleroderma and eosinophilic fascioliasis; blood flow disorders due to vasodilatation, and systemic lupus erythematosus in a mammal, comprising administering to a mammal in need of such prevention or treatment an amount of a compound of claim 1, or a pharmaceutically acceptable salt thereof, that is effective in preventing or treating such disorder or condition.

* * * * *